United States Patent [19]

Goodwin

[11] 4,085,155

[45] Apr. 18, 1978

[54] PREPARATION OF ALKYL SUBSTITUTED 1,3-DIMETHYLBENZENES

[75] Inventor: Thomas E. Goodwin, College Station, Tex.

[73] Assignee: Continental Oil Company, Ponca City, Okla.

[21] Appl. No.: 793,110

[22] Filed: May 2, 1977

Related U.S. Application Data

[63] Continuation-in-part of Ser. No. 738,931, Nov. 4, 1976, abandoned.

[51] Int. Cl.$^2$ ............................................... C07C 1/20
[52] U.S. Cl. ........................... 260/668 R; 260/668 D; 260/668 B
[58] Field of Search ............ 260/668 D, 668 R, 668 B

[56] References Cited

U.S. PATENT DOCUMENTS

| | | | |
|---|---|---|---|
| 1,977,178 | 10/1934 | Dohse et al. | 260/668 R |
| 2,419,142 | 4/1947 | Ipatieff et al. | 260/668 R |
| 2,837,584 | 6/1958 | Hoff | 260/668 R |
| 3,201,485 | 8/1965 | Kovach | 260/668 R |
| 3,894,105 | 7/1975 | Chang | 260/668 R |

OTHER PUBLICATIONS

Chem. Ab. 71:112540y, 1969.

*Primary Examiner*—Veronica O'Keefe
*Attorney, Agent, or Firm*—Bayless E. Rutherford, Jr.

[57] ABSTRACT

Alkyl substituted 1,3-dimethylbenzenes are prepared by reacting a mixture of acetone and 1-alkanols over a catalyst, which preferably is alumina, at elevated temperatures and pressures. Preferably, the product contains substantial amounts of penta- and hexaalkylbenzenes.

10 Claims, No Drawings

PREPARATION OF ALKYL SUBSTITUTED 1,3-DIMETHYLBENZENES

CROSS-REFERENCE TO RELATED APPLICATIONS

The present application is a continuation-in-part of application Ser. No. 738,931, filed Nov. 4, 1976 now abandoned.

FIELD OF THE INVENTION

The invention is in the general field of preparing polyalkylbenzenes, and particularly penta- and hexaalkylbenzenes.

BACKGROUND

Polyalkylated benzenes normally are prepared by Friedel-Crafts alkylation. Hexamethylbenzene has been prepared in good yield by the reaction of phenol and excess methanol over alumina at 320° C.[1]

[1] A. P. Krysin and V. A. Koptyug, Izvestiyr Akad. Nauk SSSR, Ser. Khim., No. 7, 1957 (1969); Chem. Abstr. 71, 112540 y (1969).

It is known that mesitylene (1,3,5-trimethylbenzene) can be prepared by reacting acetone in the vapor phase using a catalyst, such as alumina.

My invention is directed to a process for preparing penta- and hexaalkylbenzenes, and particularly penta- and hexamethylbenzenes.

Hexamethylbenzene is useful in that it can be converted to a useful polyimide. The hexamethylbenzene is oxidized to dimethylpyromellitic acid which in turn is converted to the polyimide.

The penta- and hexaalkylbenzenes are useful as lubricants and transformer oils.

PRIOR ART

A search of the prior art did not find any reference teaching the preparation of penta- and hexamethylbenzenes by reacting a mixture of acetone and methanol.

Additionally, the following references were cited against the parent application:

U.S. Pat. No. 1,977,178

This reference teaches a process for the preparation of mesitylene (1,3,5-trimethylbenzene) by dehydrating acetone using bauxite as the catalyst. Preferably, the bauxite is dehydrated.

Applicant submits that this reference is not pertinent to the preparation of penta- and hexaalkylbenzenes.

U.S. Pat. No. 2,419,142

This reference teaches a process for converting alkyl ketones to polyalkyl benzenes. In a preferred embodiment it teaches preparation of mesitylene from acetone using as the catalyst copper oxide, zinc oxide or alumina.

Again, Applicant submits that this reference does not teach the preparation of penta- and hexaalkylbenzenes.

U.S. Pat. No. 2,837,584

This reference teaches a process for preparing durene (1,2,4,5-tetramethylbenzene) from lower alkyl aromatics by an alkylation process. Applicant submits that this reference is not pertinent in that it is directed to the preparation of durene by a process which is different from Applicant's process.

U.S. Pat. No. 3,201,485

This reference teaches the preparation of polyalkylated benzenes from alkyl ketones using as the catalyst chromia-boria on alumina or chromia-zinc oxide on silica-alumina. In preferred embodiments, mesitylene is prepared and the process employs hydrogen.

Applicant submits that this reference does not teach the preparation of penta- and hexaalkylbenzenes.

U.S. Pat. No. 3,894,105

Basically, this reference teaches the preparation of durene from methanol using a particular type of alumino-silicate zeolite as the catalyst.

Applicant submits that this reference is not pertinent in that it does not teach the preparation of penta- and hexaalkylbenzene and uses an entirely different catalyst than used in Applicant's process.

In addition the following reference was cited in the parent application as being of interest.

C.A. 71, 112540 y

This reference teaches the preparation of hexamethylbenzene from phenol and methyl alcohol.

Applicant submits the reference is not pertinent in that it uses phenol whereas Applicant's process uses acetone.

BRIEF SUMMARY OF THE INVENTION

A process for preparing alkyl substituted benzenes, containing at least 5 alkyl groups, said alkyl substituted benzenes being represented by the formula

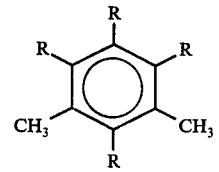

wherein R is hydrogen or a $C_1$–$C_{15}$ alkyl group, with at least three of the R substituents being alkyl groups, wherein the process comprises reacting acetone and a 1-alkanol, containing one to 15 carbon atoms, in the presence of an effective amount of a catalyst at elevated temperatures and pressures.

Preferably, the catalyst is alumina.

Preferably, the product contains both penta- and hexaalkylbenzenes.

DETAILED DESCRIPTION

Materials Used

Any commercial grade acetone can be used in my process. Of course, it is understood that higher purity acetone will give a products having fewer impurities.

Suitable alcohols for use in my process include 1-alkanols containing from 1 to 15 carbon atoms. Preferably, the alkanols contain from 1 to 10 carbon atoms. While branched-chain alkanols are suitable preferably linear alkanols are used. Also, mixtures of 1-alkanols can be used.

With regards to amounts of alkanol and acetone expressed as alkanol to acetone, on a molar basis a suitable amount is in the range of about 0.3:1 to about 15:1. On the same basis the preferred amount is in the range of about 0.5:1 to about 3:1.

Suitable catalysts for conducting my process include titanium dioxide, silica-alumina, and alumina. An example of a suitable silica-alumina catalyst is the synthetic silica-alumina catalysts used in the refining of petroleum. These catalysts contain from 85 to 95 weight percent silica (as $SiO_2$) and from 10 to 15 weight percent alumina (as $Al_2O_3$). Suitable aluminas, are those characterized as having low sodium content (e.g. less 0.05% as $Na_2O$) and a high surface area, e.g. above 250 $m^2$/gm. A particularly suitable alumina is available under the trademark CATAPAL ®, which can be obtained from the Conoco Chemicals Division of Continental Oil Company, Houston, Tex. CATAPAL ® alumina has the following typical properties:

| | |
|---|---|
| Surface Area | 260 – 400 $m^2$/gm. |
| $Na_2O$, wt. % | less than 0.01 |
| Bulk Density, about | 7.5 to 25 lb./$ft.^2$ |

The amount of catalyst is related to the liquid hour space velocity (LHSV)

$$LHSV = \frac{\text{volume of liquid per hour}}{\text{volume of catalyst}}$$

A suitable range of LHSV is about 0.1 to 1,000. A more suitable range is about 1 to 50. The preferred range is about 15 to about 40.

Process Conditions

While my process can be conducted under batch-operation conditions the nature of the process makes it preferable that it be conducted on a continuous basis. Usually the catalyst is placed in a reaction vessel, e.g. an elongated tube, and the required amount of reactants are passed through the reaction vessel at the desired temperature and pressure conditions.

Suitably the reaction is conducted at a temperature in the range of about 200° to about 550° C. Preferably, the reaction temperature is in the range of about 250° to about 550° C.

Suitably, the reaction is conducted at a pressure in the range of about 0 to about 2,000 psig. Preferably, the reaction is conducted at a pressure in the range of about 200 to about 600 psig.

The liquid hour space velocity (LHSV) has been defined in the discussion concerning the catalyst. As is known by those skilled in the art the reaction time is related to the LHSV. In order to provide a more specific teaching the reaction time should be in the range of about 0.1 to about 500 seconds, preferably about 1 to about 10 seconds.

In order to illustrate the nature of the present invention still more clearly, the following examples will be given. It is to be understood, however, that the invention is not to be limited to the specific conditions or details set forth in these examples except insofar as such limitations are specified in the appended claims.

EXAMPLE 1

This example illustrates the preparation of pentamethylbenzene and hexamethylbenzene using a 1.8 to 1 molar mixture of methanol and acetone. The catalyst was CATAPAL ® SB alumina. The reaction conditions were: 375° C., 400 psig, and LHSV = 26.5.

The results were as follows:

| Component | Feed | Product |
|---|---|---|
| methanol/acetone | 100.0 | 11.5 |
| mesityl oxide | — | 1.3 |
| mesitylene | — | 3.3 |
| isophorone | — | 0.6 |
| 3,5-xylenol | — | 0.9 |
| 2,3,6-trimethylphenol | — | 1.6 |
| pentamethylbenzene | — | 16.3 |
| 2,3,5,6-tetramethylphenol | — | 1.5 |
| hexamethylbenzene | — | 15.0 |
| unknowns | — | 48.0 |

EXAMPLE 2

This example illustrates the preparation of alkyl substituted 1,3-dimethylbenzenes, containing at least 3 alkyl groups in addition to the methyl groups, by reacting a 1.8 molar mixture of n-propanol and acetone. The reaction conditions and catalyst are the same as in Example 1. The product contains a substantial amount of propyl substituted 1,3-dimethylbenzenes containing 3 and 4 propyl substituents.

EXAMPLE 3

A mixture of alkanol and acetone in 5:1 molar ratio is pumped at a rate of 13 ml/min over a catalyst bed containing 15 ml of CATAPAL ® alumina powder, maintained at 700 psig pressure and 375° C. The product contains substantial amounts of diethyltrimethylbenzene and triethyltrimethylbenzene.

EXAMPLE 4

A mixture of 1-octanol and acetone in 2:1 molar ratio was pumped at a rate of 70 ml/min over 13 ml of silica-alumina catalyst maintained at 300° C. and 300 psig to produce a mixture containing substantial amounts of dioctyltrimethylbenzene and trioctyltrimethylbenzene.

Thus, having described the invention in detail, it will be understood by those skilled in the art that certain variations and modifications may be made without departing from the spirit and scope of the invention as defined herein and in the appended claims.

I claim:

1. A process for preparing alkyl substituted benzenes, containing at least 5 alkyl groups, said alkyl substituted benzenes being represented by the formula

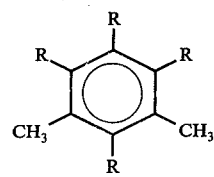

wherein R is hydrogen or a $C_1$–$C_{15}$ alkyl group, with at least three of the R substituents being alkyl groups, by a process which comprises reacting acetone and 1-alkanol, containing 1 to 15 carbon atoms, in the presence of an effective amount of a catalyst, selected from the group consisting of titanium dioxide, synthetic silica-alumina, and alumina at a temperature in the range of about 200° to about 550° C. and a pressure in the range of about 0 to about 2,000 psig, said process being characterized further in that:

a. the amount of alkanol to acetone, on a molar basis, is in the range of about 0.3:1 to about 15:1, b. the liquid hourly space velocity (volume), of liquid to catalyst, is in the range of about 0.1 to about 1,000.

2. The process of claim 1 wherein the catalyst is a synthetic silica-alumina catalyst.

3. The process of claim 1 wherein the catalyst is alumina having a surface area above about 250 m$^2$/gm. and a sodium content (as $Na_2O$) of less than 0.05 weight percent.

4. The process of claim 3 wherein:
   a. the temperature is in the range of about 250° to about 550° C.,
   b. the pressure is in the range of about 200 to about 600 psig,
   c. the liquid volume space velocity is in the range of about 1 to about 50, and
   d. the amount of alcohol is in the range of about 0.5:1 to about 3:1.

5. The process of claim 4 wherein the alumina has the following properties:

| Surface Area, about | 260 – 400 m$^2$/gm. |
| $Na_2O$, wt. % | less than 0.01 |
| Bulk density, about | 7.5 to 25 lb./ft.$^2$ |

6. The process for preparing penta- and hexa-methylbenzenes by a process which comprises reacting acetone and methanol in the presence of an effective amount of a catalyst, selected from the group consisting of titanium dioxide, synthetic silica-alumina, and alumina at a temperature in the range of about 200° to about 550° C. and a pressure in the range of about 0 to about 2,000 psig, said process being characterized further in that:
   a. the amount of methanol to acetone, on a molar basis, is in the range of about 0.3:1 to about 15:1,
   b. the liquid hourly space velocity (volume), of liquid to catalyst, is in the range of about 0.1 to about 1,000.

7. The process of claim 6 wherein the catalyst is a synthetic silica-alumina catalyst.

8. The process of claim 7 wherein the catalyst is alumina having a surface area above about 250 m$^2$/gm. and a sodium content (as $Na_2O$) of less than 0.05 weight percent.

9. The process of claim 8 wherein:
   a. the temperature is in the range of about 250° to about 550° C.,
   b. the pressure is in the range of about 200 to about 600 psig,
   c. the liquid volume space velocity is in the range of about 1 to about 50, and
   d. the amount of alcohol is in the range of about 0.5:1 to about 3:1.

10. The process of claim 9 wherein the alumina has the following properties:

| Surface Area, about | 260 – 400 m$^2$/gm. |
| $Na_2O$, wt. % | less than 0.01 |
| Bulk density, about | 7.5 to 25 lb./ft.$^2$ |

* * * * *

UNITED STATES PATENT OFFICE
CERTIFICATE OF CORRECTION

PATENT NO. : 4,085,155
DATED : April 18, 1978
INVENTOR(S) : Thomas E. Goodwin

It is certified that error appears in the above-identified patent and that said Letters Patent are hereby corrected as shown below:

Column 3, line 5, "95" should be --90--.

Column 5, line 26, "The" should be --A--.

Signed and Sealed this

Twenty-second Day of August 1978

[SEAL]

Attest:

RUTH C. MASON
Attesting Officer

DONALD W. BANNER
Commissioner of Patents and Trademarks